United States Patent [19]

Daly et al.

[11] Patent Number: 4,823,779
[45] Date of Patent: Apr. 25, 1989

[54] PENILE IMPLANT WITH COMPENSATOR

[75] Inventors: Mark D. Daly, Milwaukee; James T. Maerzke, Kenosha; Jeffrey R. Gengler, Milwaukee; Robert E. Trick, Racine, all of Wis.

[73] Assignee: Medical Engineering Corporation, Racine, Wis.

[21] Appl. No.: 50,746

[22] Filed: May 15, 1987

[51] Int. Cl.⁴ .................................. A61F 2/26
[52] U.S. Cl. .......................................... 128/79
[58] Field of Search ............................... 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,449,520 | 5/1984 | Palomar et al. | 128/79 |
| 4,523,584 | 6/1985 | Yachia et al. | 128/79 |
| 4,550,719 | 11/1985 | Finney et al. | 128/79 |
| 4,550,720 | 11/1985 | Trick | 128/79 |
| 4,572,168 | 2/1986 | Fischell | 128/79 |
| 4,574,792 | 3/1986 | Trick | 128/79 |
| 4,590,927 | 5/1986 | Porter et al. | 128/79 |
| 4,594,997 | 6/1986 | Hakky | 128/79 |
| 4,596,242 | 6/1986 | Fischell | 128/79 |
| 4,622,958 | 11/1986 | Finney | 128/79 |

FOREIGN PATENT DOCUMENTS

WO80/00302 3/1980 European Pat. Off. .......... 128/79
2163655 3/1986 United Kingdom ............. 128/79

Primary Examiner—Gene Mancene
Assistant Examiner—Cary E. Stone
Attorney, Agent, or Firm—Quarles & Brady

[57] ABSTRACT

An inflatable penile implant includes a novel compensator which both absorbs any increased pressure to protect the components of the hydraulic system from pressure damage and which permits the implant to be shortened in length without impairing its function. An improved tapered pumping chamber, improved pump valve and an improved pressure relief valve are also disclosed.

1 Claim, 3 Drawing Sheets

PENILE IMPLANT WITH COMPENSATOR

TECHNICAL FIELD

The present invention relates to inflatable implants. More particularly, it relates to a inflatable penile implant which includes a novel compensator which both absorbs sharp increases in pressure to protect the components of the implant from damage and which also permits the length of the implant to be shortened without impairing its function.

BACKGROUND OF THE INVENTION

Inflatable penile implants depend upon closed hydraulic systems to maintain a desired pressure in a pressure chamber for extended periods of time. In U.S. Pat. No. 4,353,360, an inflatable penile implant is described which includes a pressure chamber which is a non-distensible cylindrical chamber. When the pressure chamber is pressurized, it becomes rigid and the penis assumes an erectile state.

The components of the hydraulic system of inflatable penile implants are made of the suitable materials and are designed to operate reliably under conditions which normally might be encountered. There are, however, occasions in which the pressure within the pressure chamber may greatly exceed that for which the components were designed. For example, when the implant and its inflated pressure chamber are accidentally bent or squeezed, a much higher pressure than normal can be generated within the hydraulic system. Such increased pressures can cause damage to the hydraulic system components and cause the implant to fail.

In the Finney U.S. Pat. No. 4,622,958, issued accumulator which increases in volume to absorb and compensate for any increased pressures that might otherwise damage the hydraulic system components.

Another problem which can accompany the use of inflatable penile implants is getting the right size inflatable implant into some patients. Although the surgeon carefully takes measurements and selects the proper size implant for a patient, with some patients it is still difficult to maneuver the implant into the corpora cavernosum. With such patients it would be helpful if the implant could be shortened even slightly for insertion into the corpora without impairing its function.

Still another problem that can occur with inflatable implants is tissue encapsulation which can cause the implant to become constrained or shortened so that it cannot reach its full length. It would be helpful to have an implant the functioning of which would not be impaired even if the implant became constrained in length.

SUMMARY OF THE INVENTION

It is an object of the present invention to disclose an implant which includes a compensator for absorbing and compensating for pressure peaks which might otherwise damage the hydraulic systems of the penile implants.

It is a further object to disclose an implant with a compensator for temporarily shortening a penile implant for ease of insertion into a patient.

It is still further an object to disclose an implant with a compensator that permits the implant to function properly even if its length is constrained as by encapsulation.

The compensator of the present insertion is a generally cylindrical member which is interposed between the pressure chamber of the implant and a pressure relief valve. The compensator has one end for connection to the pressure chamber of the implant, an intermediate flexible hinge portion of expandable or distensible material and the other end for connection to the pressure relief valve.

The intermediate distensible portion will expand outwardly when the normal working pressure of the implant has been exceeded to increase the internal volume of the compensator thus absorbing and compensating for the increased pressure. The intermediate portion also serves as a hinge which permits the implant to be reduced in overall length as when it is longitudinally constrained without impairing its function.

In a preferred embodiment, the compensator is a generally cylindrical member of molded high durometer silicone elastomer having one end which is of a relatively large diameter, a double opposed radii intermediate portion and a second end which is relatively smaller in diameter than the first end. When the length of an implant having the preferred compensator is constrained or reduced the two ends are moved closer together with the intermediate portion serving as a folding hinge.

An implant equipped with the compensator of the present invention will stay rigid even after an accidental and/or abnormal bend angle is experienced. In addition, it is easier to insert a proper size implant with a compensator and the implant with a compensator will be able to function even if tissue encapsulation later occurs because the penile length will be adjusted automatically. Thus, the need for reoperations to adjust sizing or to remedy the effects of encapsulation can be eliminated Additional objects of the invention are to disclose a penile implant with an improved tapered pump tip, an improved pump valve and an improved pressure relief valve.

Further objects and advantages to the invention will become apparent to those skilled in the art from the description of the preferred embodiment and the drawings.

BEST MODE OF CARRYING OUT THE INVENTION

The preferred penile erectile system is of the type disclosed in U.S. Pat. No. 4,399,811. It comprises a pair of the penile implants shown in FIG. 1 which are implanted in the corpora cavernosa of a penis. The two implants are identical, therefore, only one will be described in detail.

Figure 1:
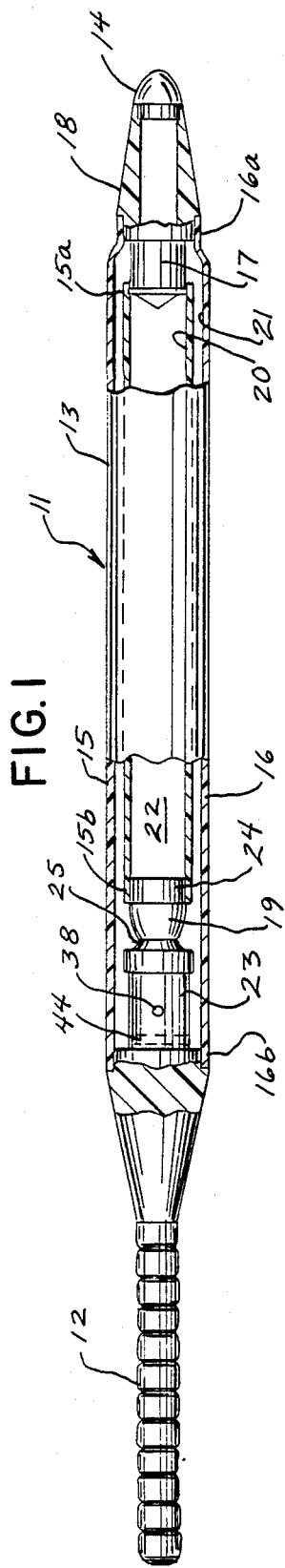
FIG. 1 is a side view, partly in section, of a penile implant including the preferred embodiment of the compensator of the present invention.

As seen in FIG. 1 of the drawings, the implant 11 has a trimmable, proximal stem 12, an intermediate cylindrical portion 13, and a distal tip 14. The stem 12 which is of a relatively stiff material is implanted in the root end of a corpus cavernosum and the flexible cylindrical portion 13 and the tip 14 are implanted in the portion of the corpus cavernosum in the pendulous penis. Each of the two implants is positioned in a separate corpus cavernosum of the penis.

The intermediate cylindrical portion 13 of the implant 11 includes a pair of concentric cylindrical sleeves 15 and 16. The sleeve 15 is attached at one end 15a in a fluid tight manner to a valve 17 of a pump 18. The other end 15b of the sleeve 15 is connected to the compensator 19. The sleeve 15 is of an inelastic material so that the chamber 20 which it forms with the valve 17 and pump 18 is non-distensible even when pressurized. The sleeve 15 also cooperates with the sleeve 16 which is spaced outwardly from the sleeve 15 to form an outer reservoir chamber 21. One end 16a the sleeve 16 is attached to the pump 18 and the other end 16b is attached to the stem 12. The sleeve 16 may be made of a distensible material such as non-reinforced silicone rubber. The necessary fluid tight seals between the various components may be made with a silicone adhesive or by other suitable means.

As seen in FIG. 1, when the implant 11 is in a pressurized state the chamber 20 is completely filled and the chamber 21 is substantially filled with a non-compressible hydraulic fluid 22 which may be a biocompatible fluid such as saline or a free flowing silicone gel. As seen in FIG. 1, the intermediate cylindrical portion 13 is straight and rigid as the result of the non-distensible inner chamber 20 becoming a pressure chamber completely filled with fluid under pressure. Thus, the penis then assumes an erectile position. In the non-pressurized state, both of the chambers 20 and 21 are substantially filled with fluid and the soft, flexible, intermediate cylindrical portion 13 of the implant 11 flexes and permits the penis to assume a substantially normal, flaccid position.

The valve 17, the compensator 19 and an improved pressure relief valve 23 will be described hereinafter.

Figure 4:
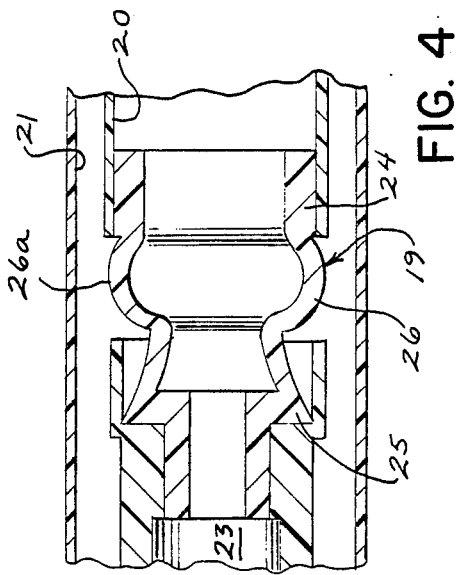
FIG. 4 is a view similar to FIG. 2, showing the condition of the compensator when the pressure chamber of the implant is subjected to pressures above the working pressure.
Figure 2:
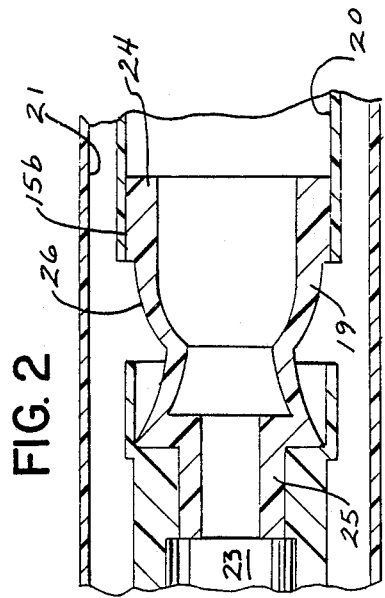
FIG. 2 is a enlarged partial side view of the implant of FIG. 1, showing the condition of a compensator of a full length implant.

Turning first to FIGS. 1 to 4 the preferred embodiment of the compensator 19 can be seen to be located between the pressure chamber 20 and the pressure relief valve 23. As seen therein the compensator has a relatively large first end 24 which is connected to one end of the pressure chamber 20. The other end 25 of the compensator 19 is connected to the pressure relief valve 23. The intermediate portion 26 of the compensator 19 is a double opposed radii shaped cylinder. As can be seen in FIGS. 1 and 2 when the implant 11 is its full length and at working pressure or below, the intermediate portion 26 of the compensator 19 is in its normal unexpaded state. However, as seen in FIG. 4, when the pressurized implant 11 is bent or otherwise subjected to increased external pressure, the intermediate portion 26 of the compensator 19, which is more distensible than the sleeve 15, is expanded outwardly because of the increased pressure in the pressure chamber 20.

The wall 26a of the intermediate portion 26 is constructed of an elastomeric material, preferably a high durometer silicone elastomer, which does not stretch until an internal pressure exceeding the normal working pressure is exceeded. When the pressure drops to or below the working pressure, the wall 26a resumes its original non-expanded condition seen in FIGS. 1 and 2. The distendability or elasticity of the wall 26a can be controlled in any number of acceptable ways. The wall may be made of a more elastomeric material than the rest of the compensator or it may be made thinner, so that it will expand more easily when the working pressure is exceeded. To prevent over-stretching of the wall, the elastomeric material of the wall may also be reinforced with crimped threads which limit the expansion as described in U.S. Pat. No. 4,201,202.

Figure 3:
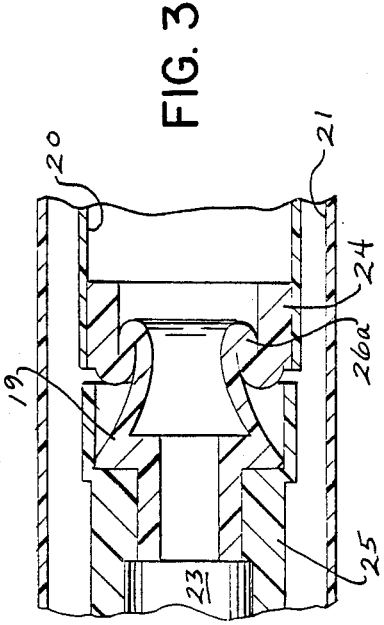
FIG. 3 is a partial view similar to FIG. 2, showing the condition of the compensator when the implant is shortened.

In FIG. 3, the compensator 19 is shown with the intermediate portion 26 serving as a hinge which folds upon itself so that the ends 24 and 25 are closer to each other. This is the form the compensator 19 takes when the implant 11 is shortened for ease of insertion into a patient; it may also take this form when the length of the selected implant 11 is slightly longer than the patient's corpus cavernosum or it is constrained after implanting, for example, as may result from tissue encapsulation.

Figure 5:
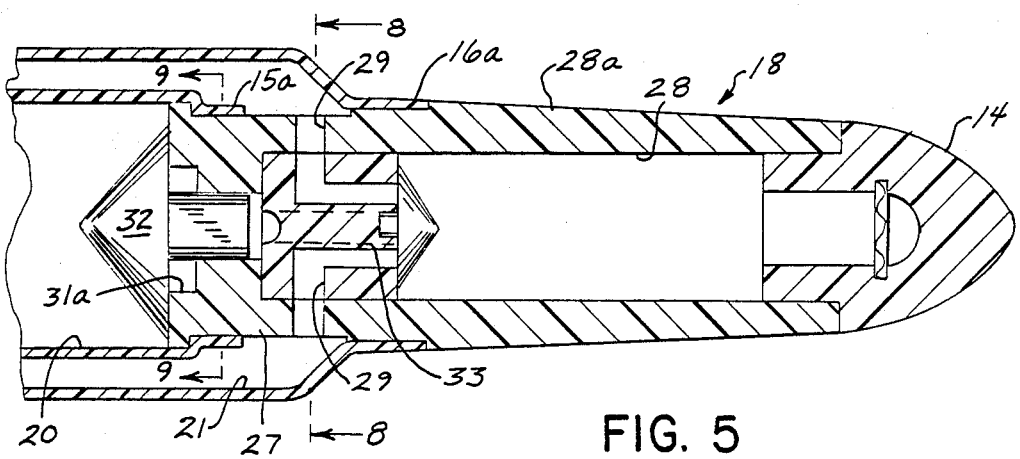
FIGS. 5 to 9 are enlarged sectional views of the pump valve of the implant of FIG. 1; and, FIGS. 10 and 11 are enlarged sectional views of the pressure relief valve of the implant of FIG. 1.

Turning next to FIGS. 5 to 9, the valve 17 is seen to comprise a valve housing 27 which separates the chambers 20 and 21 from a tapered pumping chamber 28 adjacent the tip 14. An inlet passage 29 in the housing 27 leads from the outer chamber 21 to the pumping chamber 28. A mushroom like inlet valve 30 controls the flow of fluid 22 from chamber 21 to pumping chamber 28. An outlet passage 31 (best seen in FIG. 6) leads from outside the periphery of the cap 30a of the inlet valve 30 in the pumping chamber 28 to the pressure chamber 20. The exit of the passage 31 which leads to the chamber 20 is closed by a mushroom like outlet valve 32. When the pump 18 is not in use both the valves 30 and 32 are closed as seen in FIG. 5.

Figure 6:
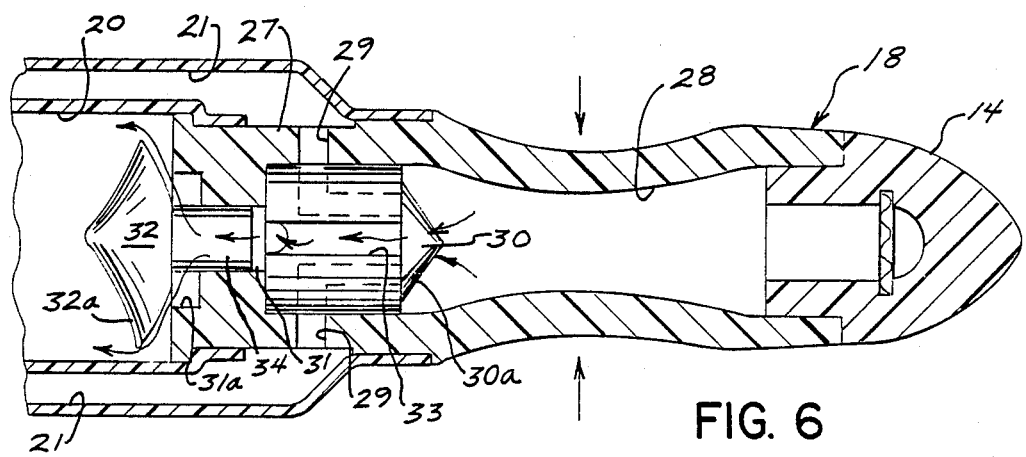

When as seen in FIG. 6, the pump 18 is activated by squeezing the tapered pumping chamber 28 the passage 29 is closed by the inlet valve 30. When the squeezing is stopped and the walls of the pump 18 flex outwardly the fluid pressure in the outer chamber 21 exceeds that in the pumping chamber 28 and the lip of the cap 30a of the inlet valve 30 is lifted off its seat permitting fluid to enter the pumping chamber 28 via the inlet passage 29 (seen best in FIG. 7).

The outlet valve 32 of the pump 18 normally closes the passage 31. The valve 32 forms a seal about the exit 31a of passage 31 when the pressure in the pressure chamber 20 exceeds that in the pumping chamber 28. When the tapered resilient wall 28a of the pumping chamber 28 is squeezed the fluid pressure in the pumping chamber 28 exceeds that in pressure chamber 20 and the lip of the valve 32 is moved out of sealing engagement with its seat on the housing 27 allowing fluid to flow from the pumping chamber 28 and into the pressure chamber 20 via two passageways 33 located outside the periphery of the cap of the valve 30. The passageways 33 seen best in FIGS. 6 and 8) form part of the passage 31 which also includes the exit of passageway 34 (seen best in FIG. 9) which is closed by the back of the cap 32a of the valve 32.

The implant 11 is pressurized by repeatedly squeezing the pumping chamber 28 to force the fluid 22 from the pumping chamber 28 into non-distensible pressure chamber 20 under pressure. When the pressure chamber 20 is sufficiently pressurized and rigid, the pumping action is stopped whereby the exit of the passage 31 is closed by pressure of the fluid 22 in pressure chamber 20 upon the cap of mushroom outlet valve 32.

Figure 7:
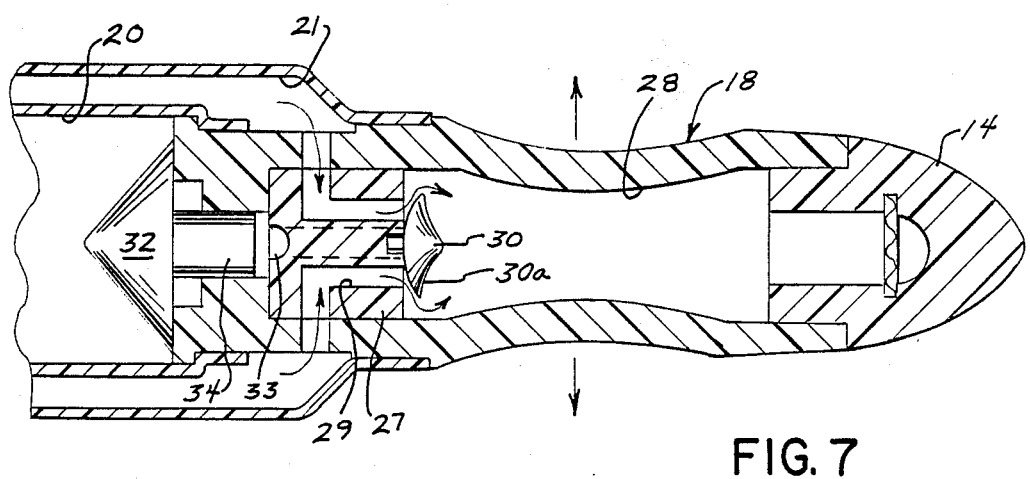
Figure 8:
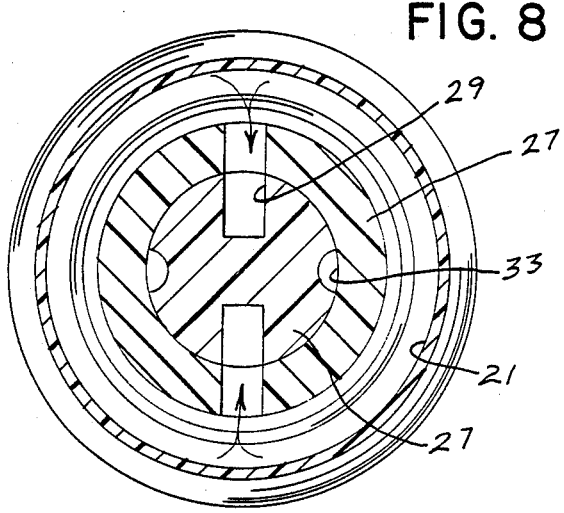
Figure 9:
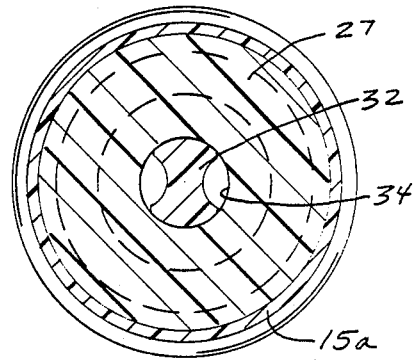

The direction the liquid flows when the pump is squeezed is shown by arrows in FIG. 6 and the direction the liquid flows when the pump chamber recovers its normal state is shown by arrows in FIG. 7. The improved pump valve 17 more effectively prevents pump bypass than prior art valves.

Figure 10:
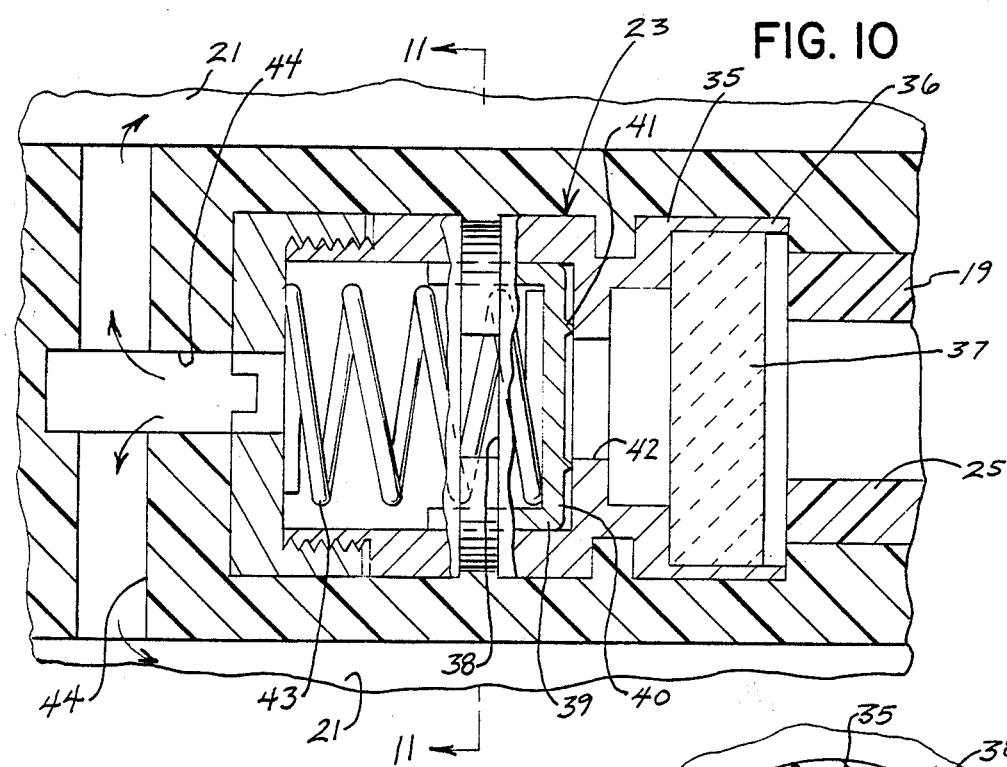
Figure 11:
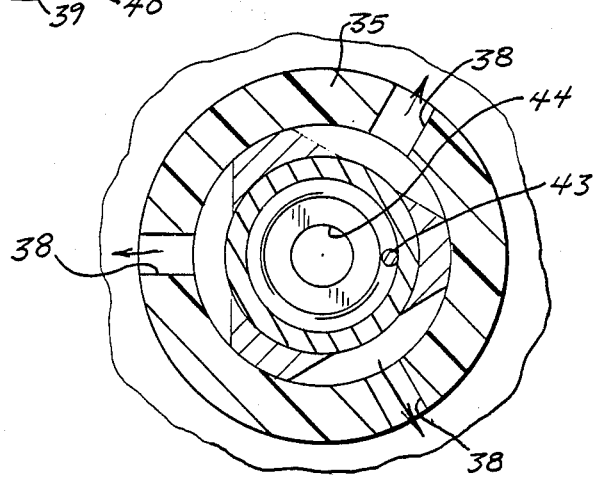

The improved pressure relief valve 23 will be described in connection with FIGS. 1, 10 and 11.

In FIG. 1, it can be seen that the pressure relief valve 23 is located between the compensator 19 and the stem 12. Turning to FIGS. 10 and 11, it can be seen the valve 23 includes a hollow cylindrical valve housing 35 having an inlet 36 at one end 37 and three outlets 38. Interposed in the housing 35 between the inlet 36 and the outlet 38 is a close fitting piston 39 which has a piston face 40 with a raised annular knife edge seal 41. As seen in FIG. 10 the seal 41 is seated against an internal annular flange 42 in the housing preventing flow out the outlets 38. The seal 41 is maintained seated by a precalibrated spring 43. The area of the housing 35 behind the piston 39 is in communication with the chamber 21 via a passageway 44.

When there is a fluid pressure in the pressure chamber 20 which is greater than that which can be handled by the compensator 19 the fluid pressure on the area of the face 40 within the seal 41 of the piston 39 will begin to move the seal 41 off its seat on the flange 42. As this occurs the area of the piston face 40 outside the seal 41 and the sides of the piston 39 are exposed to the force so that a much greater force is available to move the piston 39 further back to expose the outlets 38 (e.g. 1500 cm/$H_2O$). When this much larger force is present the piston 39 moves back quickly and the liquid 22 rapidly flows out the outlets 38 into the reservoir chamber 21. As the piston 39 moves back the liquid 22 in the housing 35 behind the piston 39 also will flow via passageway 44 into the chamber 21 as shown by the arrows in FIG. 10.

Because of the larger area of the piston 39 subjected to fluid pressure when the valve 23 is open the seal 41 will not be seated on the flange 42 until the pressure sensed by the piston 39 is exceeded by the bias of the spring 43 which is much lower than the opening pressure (e.g. 300 cm $H_2O$). When this occurs the space in the housing 35 behind the piston 39 will once again be filled with liquid 22 from the chamber 21. From the foregoing, it is apparent that the improved valve has two characteristic pressures; a high cracking pressure which causes the valve to quickly open and a much lower seating pressure which causes it to close. As a result, the implant 11 can be quickly and more totally deflated by bending and the valve 23 will not close until the pressure has dropped substantially thereby giving the implant better flaccidity.

All the components of the described implants are preferably made of biocompatible materials having the necessary properties to function as intended.

The non-distensible inner chamber 20 of the penile implants must when pressurized provide rigidity sufficient to maintain the penis in an erectile position. Therefore, it must be of sufficient volume and size to perform this function either alone or in combination with another implant. In contrast, the outer chamber 21 serves primarily as a reservoir of pressurizing fluid for the inner chamber and is sized accordingly. The exact dimensions of the inner and outer chambers are not critical as long as they are adequate to provide their desired function.

The sleeve 15 which forms the wall of the "non-distensible" pressure chamber 20 must be relatively inelastic and is preferably made of a dacron mesh or fabric covered with silicone material that will not stretch or which will stretch to a limited amount when filled with fluid and pressurized.

The sleeve 16 may be distensible or non-distensible. It is preferably less distensible than the wall of the accumulating chamber. The diameters of the sleeves 15 and 16 can vary but are normally sized so that the implant in the non-pressurized state will fill the corpus cavernosum. It will be appreciated that the terms distensible, non-distensible and inelastic an intended to cover any materials which possess the desired properties which enable them to provide the described functions.

The proximal stem 12 of the implant preferably has a Shore A hardness of about 70, the tip 14 has a Shore A hardness of about 20, and each of the materials has sufficient tensile strength for its intended use.

The term "substantially filled" as used herein to describe the fluid content of a chamber in the penile implant means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

All the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the implant of FIG. 1 is through an incision made in the penis. After appropriate incision, each corpus cavernosum is dilated distally and proximally to accept the implants. The appropriate anatomical measurements are made to insure that the proximal end of the implant or implants will be positioned is the proximal crus. Preferably, the pump is located in the distal corpra near the glans. An implant having an appropriately sized intermediate section and distal tip is inserted into each of the corpus cavernosum of the penis. If necessary the implant can be shortened slightly by pushing the tip 14 back towards the stem 12 which causes the compensator to fold back upon itself as shown in FIG. 4. The difference in length of the implant between the full and shortened length although small can make in important difference in fitting the patient with the proper length implant. When properly positioned the distal tip of the implant is in the glans end of the corpus cavernosum and the stem is anchored in the root end of the corpus cavernosum.

The identical procedure is performed on the other side of the penis to complete the surgical procedure. The stems of the two implants preferably will diverge laterally to accommodate the anatomy, to provide lateral stability to the penis and to help prevent rotation of the implants. The incision is then closed.

It will be understood that the foregoing description has been for purposes of illustration and that the accumulating means of the present invention may be used with other designs of inflatable implants than that described. Therefore, the invention is not to be limited except by the claims which follow.

We claim:

1. In a self-contained penile implant which comprises an elongated, generally cylindrical smooth walled member having a conical tip and an anchoring base, said member containing in its interior a pressure chamber, a reservoir for pressurizing fluid, a pump operatively connected to the reservoir and pressure chamber for transferring fluid from the reservoir to the pressure chamber, a relief valve operatively connected to the pressure chamber for monitoring the pressure in the pressure chamber at a safe level and a compensator which absorbs sharp pressure peaks in the pressure chamber, the improvement which comprises a generally cylindrical compensator having a relatively large diameter first end connected to the pressure chamber, a relatively smaller second and connected to the relief valve and a double opposed radii intermediate section extending between the first and second ends, said intermediate section being flexible so that the overall length of the cylindrical member can be reduced without disrupting its smooth outer wall by moving the first end of the compensator back towards the relief valve and over the intermediate section.

* * * * *